United States Patent
Arbisser et al.

(10) Patent No.: US 10,660,743 B2
(45) Date of Patent: May 26, 2020

(54) INTRAOCULAR LENS AND METHODS FOR IMPLANTING THE SAME

(71) Applicants: Lisa Brothers Arbisser, Sarasota, FL (US); Gholam Peyman, Sun City, AZ (US)

(72) Inventors: Lisa Brothers Arbisser, Sarasota, FL (US); Gholam Peyman, Sun City, AZ (US)

( * ) Notice: Subject to any disclaimer, the term of this patent is extended or adjusted under 35 U.S.C. 154(b) by 0 days.

(21) Appl. No.: 16/140,801

(22) Filed: Sep. 25, 2018

(65) Prior Publication Data

US 2020/0093588 A1    Mar. 26, 2020

(51) Int. Cl.
*A61F 2/16* (2006.01)
*A61F 9/007* (2006.01)
*A61F 9/008* (2006.01)

(52) U.S. Cl.
CPC ............ *A61F 2/1613* (2013.01); *A61F 9/008* (2013.01); *A61F 9/00754* (2013.01); *A61F 2002/1683* (2013.01); *A61F 2002/16901* (2015.04); *A61F 2002/16905* (2015.04); *A61F 2009/0087* (2013.01); *A61F 2220/0008* (2013.01); *A61F 2250/0067* (2013.01)

(58) Field of Classification Search
CPC ............ A61F 2/1613; A61F 2002/1683; A61F 9/00754
See application file for complete search history.

(56) References Cited

U.S. PATENT DOCUMENTS

| | | | |
|---|---|---|---|
| 4,437,194 A * | 3/1984 | Hahs | A61F 2/16 623/6.51 |
| 4,463,458 A * | 8/1984 | Seidner | A61F 2/16 623/6.43 |
| 4,790,845 A * | 12/1988 | Grendahl | A61F 2/16 623/6.51 |
| 2005/0015143 A1* | 1/2005 | Willis | A61F 2/1608 623/6.36 |
| 2012/0203338 A1 | 8/2012 | Jain | |
| 2014/0074074 A1 | 3/2014 | Dick | |

* cited by examiner

*Primary Examiner* — Leslie Lopez
(74) *Attorney, Agent, or Firm* — Wood, Philips, Katz, Clark & Mortimer

(57) ABSTRACT

An intraocular lens has central lens body at least one haptic extending from the central lens body. The haptic has a lobular configuration. The lens body and the haptic having a folded configuration for implantation within the eye. The lens having a first deployed configuration wherein the lens body is positioned at a location substantially behind sealed anterior and posterior portions of the lens capsule with the at least one haptic positioned at a location substantially over top of the sealed anterior and posterior portions of the lens capsule. The lens having a second deployed configuration wherein the lens body is positioned at a location substantially in front of the sealed anterior and posterior portions of the lens capsule with the at least one haptic positioned at a location substantially over behind the sealed anterior and posterior portions of the lens capsule.

12 Claims, 5 Drawing Sheets

Fig. 6
Fig. 7
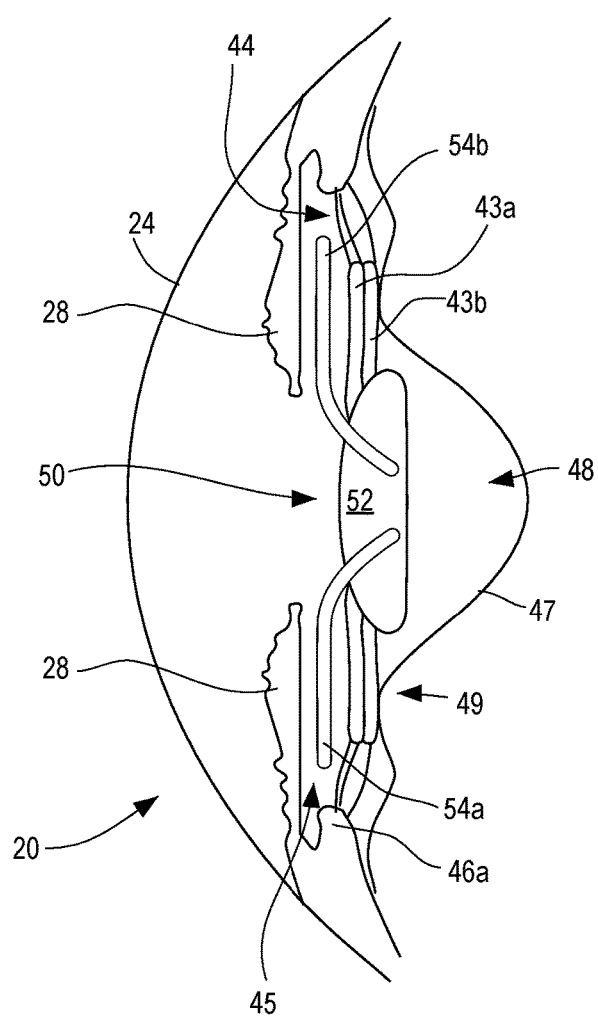
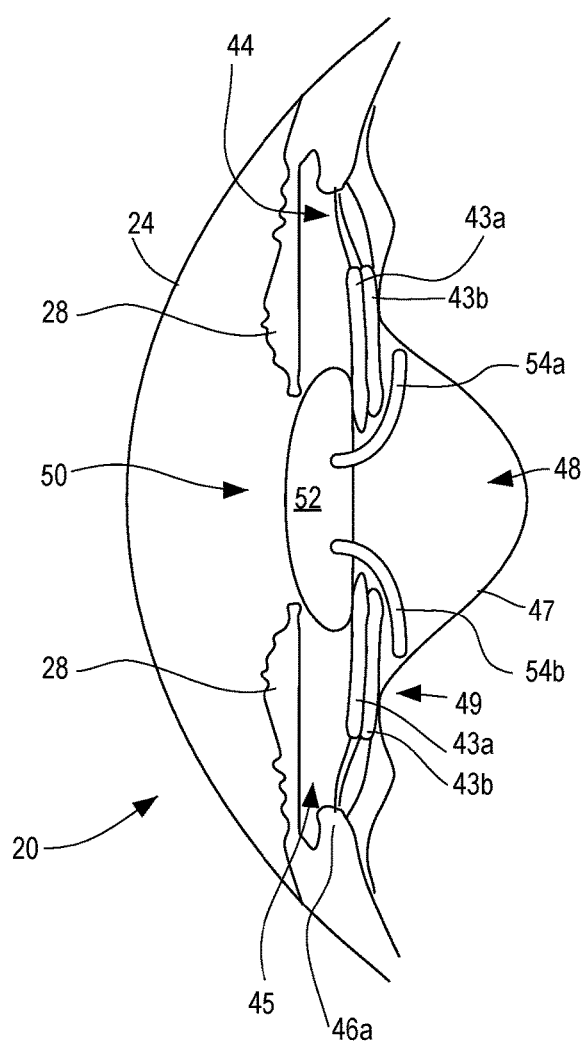

INTRAOCULAR LENS AND METHODS FOR IMPLANTING THE SAME

FIELD OF THE INVENTION

The present invention relates generally to the field of ophthalmic surgery, and more particularly, to an improved intraocular lens and improved methods for implanting an intraocular lens into the human eye.

BACKGROUND OF THE INVENTION

Cataract is one of the most common causes of blindness. Approximately 20.5 million (17.2%) Americans have a cataract in either eye, and these numbers are rising. Cataract is most commonly seen between the ages of 45-64, with a lower prevalence in males than in females. Its symptoms are manifested by progressive cloudiness of crystalline lens of the eye, leading to glare, myopic shifts, monocular diplopia, and gradual loss of vision. The comorbidities are environmental conditions such as UV exposure, altitude, occupation, diet, smoking, alcohol, medication such as steroids and diseases such as ocular inflammation (uveitis) diabetes mellitus and hypertension, as side effects of x-ray radiation and in children traumatic eye injuries and genetic predisposition. The cataract is classified depending on the stage of the lens opacification as incipient, immature, and mature and hypermature, or the location of lens opacities as cortical, nuclear, posterior subcapsular.

The treatment for cataract is surgical removal of the involved lens and is achieved by various methods. It is done under a regional anesthesia, topical anesthesia, retrobulbar anesthesia and peribulbar anesthesia, etc.

One method of treatment is intracapsular cataract extraction ("ICCE") in which the entire lens including the lens capsule is removed in one piece. This requires a relatively large 7-10 mm corneal incision through which the lens is expressed out of the eye. The procedure is seldom performed because of its numerous complications of corneal keratopathy, vitreous loss, wound leak, iris incarceration, high astigmatism, post-operative inflammation, cystoid macular edema, retinal detachment and high rate of the infection and corneal complications (bullous keratopathy). Following the operation, patients have been prescribed thick refractive glasses, which may be difficult to maintain on the patient's nose. The patients of this operation have been prone to falling when going down the stairs, and fractured bones were not an uncommon problem in these patients, even increasing the patient's mortality.

Another method of cataract treatment is extracapsular cataract extraction ("ECCE"), a procedure in which the lens cortex and nucleus is removed by an aspiration and irrigation system after removal of a part of the anterior capsule, while the rest of the capsule remains in place. This procedure has been performed most often in children having congenital cataract to avoid disrupting the posterior capsule to prevent vitreous loss. The surgery has been associated with serious post inflammatory response, glaucoma, proliferation of lens epithelial cells producing severe capsular opacification and fibrosis, and potentially retinal detachment when the posterior capsule has been inadvertently violated.

Yet another method of cataract treatment is extracapsular cataract extraction with phacoemulsification combined with intracapsular implantation of an acrylic intraocular lens ("IOL"). In this procedure, the lens cortex and nucleus are removed through a relatively small corneal incision, between about 4 mm to 5 mm in diameter, and an anterior capsulotomy. Then, an ultrasonically driven needle is used to emulsify the lens cortex and nucleus, which are then removed by an irrigation/aspiration of fluid and the lens cortical material. Subsequently, a folded IOL is implanted inside the lens capsule through a small corneal incision. While this concept has brought significant improvement to the technique of cataract surgery and benefit for the patient, the remaining lens epithelial cells have been found to attach to the anterior capsule, often proliferating posteriorly to produce a posterior capsular cloudiness and fibrosis which reduces post-operative visual acuity in the patient. Treatment of this complication involves either an yttrium aluminum garnet ("YAG") laser capsulotomy, or the removal of the part of the posterior capsule with a vitrectomy instrument by cutting and removing central part of the posterior capsule and the vitreous in order to clear the optical media. This procedure has been done routinely in the developed countries, however, it is not easily done in developing countries with a large cataract population because of the cost of a YAG-laser and/or the difficulty for the patient to return to a surgery center for an additional surgery.

An alternative procedure is to perform a limited central anterior and posterior capsulotomy in a single procedure, and the lens optic is implanted in the space of Berger located between the posterior lens capsule and anterior hyaloid membrane, while the lens haptics remain substantially in front of the lens capsule located in the posterior chamber contacting the ciliary body. When done properly, this procedure leaves a clear optical media in one surgical session without the need for subsequent need for the posterior capsulotomy. The lens capsule folds upon itself in this procedure.

In general, IOL implantation has a decades long history of biocompatibility in the eye. The IOLs are made from polymeric materials such as PMMA, silicone, hydrogel, polyvinylidene fluoride, or in combination with collagen as Collamer, multifocal IOLs are effective in providing near and far vision after cataract surgery. Toric IOLs are used to correct corneal astigmatism, such as the Alcon acrylic toric IOLs or the Johnson and Johnson Tecnis Toric 1-piece IOL.

Despite the advances in cataract surgery and the construction of the new IOLs, there are still some problems the patients have to deal with, that affect their visual satisfaction in the post-operative period.

For example, the IOLs can tilt either in a horizontal or vertical direction inducing great dissatisfaction for the patient. This happens frequently if the capsulotomy is not done properly or the lens zonulas are genetically affected in diseases such as in patients with Marfan syndrome, Morgagnian cataract, high myopia, or after traumatic injuries where the zonulas can become weak or broken, and the incomplete or partial lens zonulae contribute to a tilted IOL.

The IOLs can tilt or settle in the post-operative period as a result of capsular fibrosis after cataract surgery, for example, if the haptic and optics are inside the capsular bag and an uneven pressure is generated as a result of capsular fibrosis or a large capsulotomy.

IOLs seldom have a perfect refractive power to create an emmetropic refraction after surgery. In majority of cases the IOLs refractive power is off by plus or minus 0.5 D power or more, which is not easy to correct if the IOLs are multifocal lenses.

Lens centration is very important for multifocal lenses, otherwise patients are not satisfied with their vision and a lens exchange may be needed.

Children's eyes and myopic eyes grow significantly, requiring removal of the IOL and their replacement.

Capsular opacification occurs after the cataract surgery when the lens epithelial cells, located behind the anterior capsule, start proliferating inside the lens capsule to fill the empty space left inside the capsule after cataract extraction while the post-operative inflammatory response persists.

A need remains for a patient to have only a single operation to correct the patient's vision over the lifetime of the patient, even for patients that are infants or minors.

SUMMARY OF THE INVENTION

The inventor of the present invention has discovered an improved intraocular lens construction for implantation into a human eye and novel methods for implanting the improved intraocular lens within the human eye.

According to one aspect of the present invention, an intraocular lens is implanted into a human eye. The method includes the step of implanting the intraocular lens in a human eye having a lens capsule with an anterior portion and a posterior portion, a natural lens nucleus, and a cortex. The method includes the step of performing a capsulotomy of the anterior portion of the lens capsule and the step of removing the natural lens nucleus and cortex from the lens capsule. The method further includes the steps of performing a capsulotomy of the posterior portion of the lens capsule and the step of sealing the anterior and posterior portions of the lens capsule together.

In yet another aspect of the invention, the method includes the step of implanting an intraocular lens having a central lens body to locate the central lens body behind the sealed anterior and posterior portions of the lens capsule in Berger's space.

In still another aspect of the invention, the method includes the step of implanting an intraocular lens having a central lens body to locate the central lens body in front of the sealed anterior and posterior portions of said lens capsule.

According to yet another aspect of the invention, the anterior and the posterior portions of the lens capsule are sealed together by injecting a bio-compatible adhesive between the anterior and said posterior portions of the lens capsule. In another form of the invention, the method includes the step of applying ultraviolet radiation to the adhesive between the sealed anterior and posterior portions of the lens capsule.

In another form of the invention, the method includes the step of injecting an anti-inflammatory agent with the adhesive.

In still another form of the invention, the method further includes the additional steps of: (a) implanting a first intraocular lens having a central lens body to locate the central lens body against the sealed anterior and posterior portions of the lens capsule; and (b) implanting a second intraocular lens in front of the first intraocular lens such that the first and second intraocular lenses are in a non-contacting relationship in the eye.

According to another aspect of the present invention, an intraocular lens is implanted into a human eye. The lens having a central lens body and at least one haptic, wherein the central lens body has a refractive index. The method includes the step of implanting the intraocular lens in the eye. The method further includes the step of applying a femtosecond laser to the central lens body, while the lens body is implanted within the eye, to change the refractive index of the lens body.

In accordance with another aspect of the present invention, an intraocular lens is provided, the lens having an optic or lens body for vision correction of a patient. The lens including at least one haptic extending from the lens body. The at least one haptic having a lobular configuration with (i) a first end connected to the lens body at a first point or location, and (ii) a second end connected to the lens body at a second point or location. The second location is spaced from the first location on the lens body. The lens body and the at least one haptic have a folded configuration for being implanted in the eye. The lens body and the at least one haptic further have at least one of the following deployed configurations: (i) a first deployed configuration wherein the lens body is positioned at a location substantially behind sealed anterior and posterior portions of the lens capsule with the at least one haptic positioned at a location substantially overtop of the sealed anterior and posterior portions of the lens capsule; or (ii) a second deployed configuration wherein the lens body is positioned at a location substantially overtop of the sealed anterior and posterior portions of the lens capsule with the at least one haptic positioned at a location substantially beneath the sealed anterior and posterior portions of the lens capsule.

In still another form of the invention, the intraocular lens includes a pair of haptics extending from the lens body in a bi-lobular configuration, wherein each of the haptics form a closed loop with the lens body.

In still another form of the invention, the lens defines an anterior surface and a posterior surface, the posterior surface defining a plane, and the pair of haptics extending substantially out of the plane.

In another aspect of the invention, the lens body is formed from a transparent polymer with a surface treatment to make the lens body hydrophobic, hydrophilic, or amphiphilic.

In one aspect of the invention, the intraocular lens is provided in combination with a secondary intraocular lens. The intraocular lens and the secondary intraocular lens being arranged in a non-contacting, spaced-apart configuration in the eye.

In still another aspect of the invention, a first portion of the lens body is formed from a first polymer and a second portion of the lens body is formed from a second polymer, wherein the second polymer is softer than the first polymer.

Other features and advantages of the present invention will become readily apparent from the following detailed description, the accompanying drawings, and the appended claims. Better understood with reference to the accompanying figures and detailed description.

BRIEF DESCRIPTION OF THE DRAWINGS

FIG. 5 shows the central lens body tucked behind the anterior and posterior capsule and the lens haptics located overtop of the anterior and posterior capsule;

FIG. 6 is an enlarged, side elevation diagrammatic view of the intraocular lens shown in FIG. 3 implanted within the human eye, and FIG. 6 shows the central lens body tucked behind the anterior and posterior capsule and the lens haptics located overtop of the anterior and posterior capsule;

FIG. 7 is an enlarged, side elevation diagrammatic view of the intraocular lens shown in FIG. 3 implanted in an alternative configuration within the human eye, and FIG. 7 shows the central lens body located overtop of the anterior and posterior capsule and the lens haptics tucked behind the anterior and posterior capsule;

FIG. 8 illustrates the location of the lens body relative to the lens capsule in the first configuration of FIG. 6 (solid line) and further illustrates the location of the lens body relative to the lens capsule in the alternative configuration of FIG. 7 (phantom line)

DETAILED DESCRIPTION OF THE PREFERRED EMBODIMENTS

Figure 1:
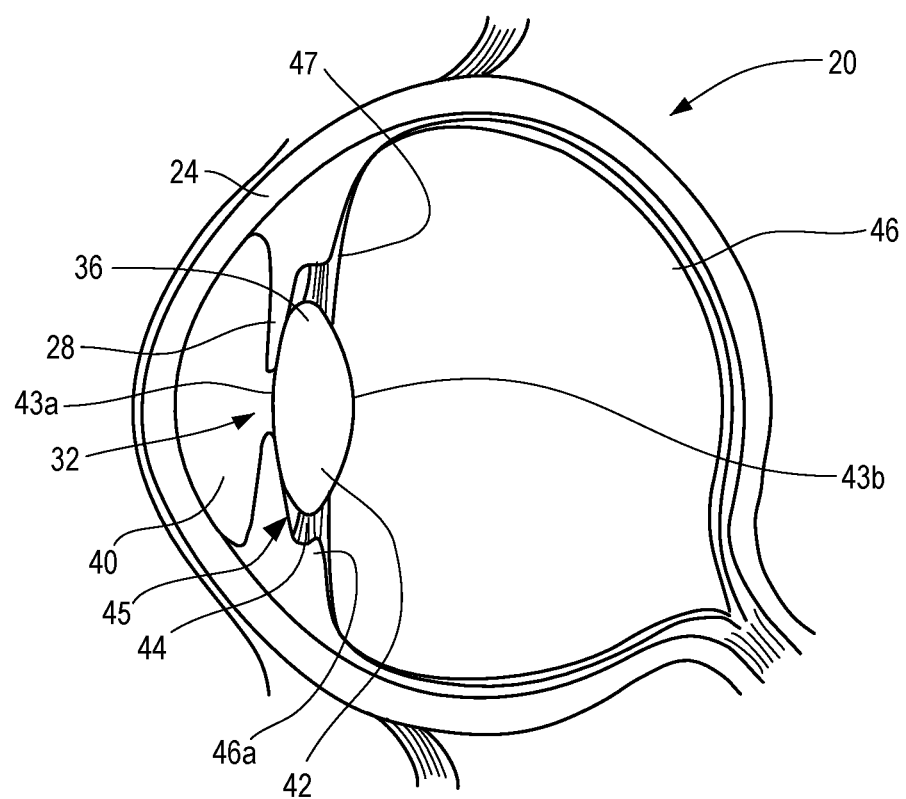
FIG. 1 is an enlarged, diagrammatic view of a human eye

While the present invention is susceptible of embodiment in various forms, there is shown in the drawings and will hereinafter be described a presently preferred embodiment of the invention, with the understanding that the present disclosure is to be considered an exemplification of the invention, and is not intended to limit the invention to the specific embodiment illustrated.

Figure 2:
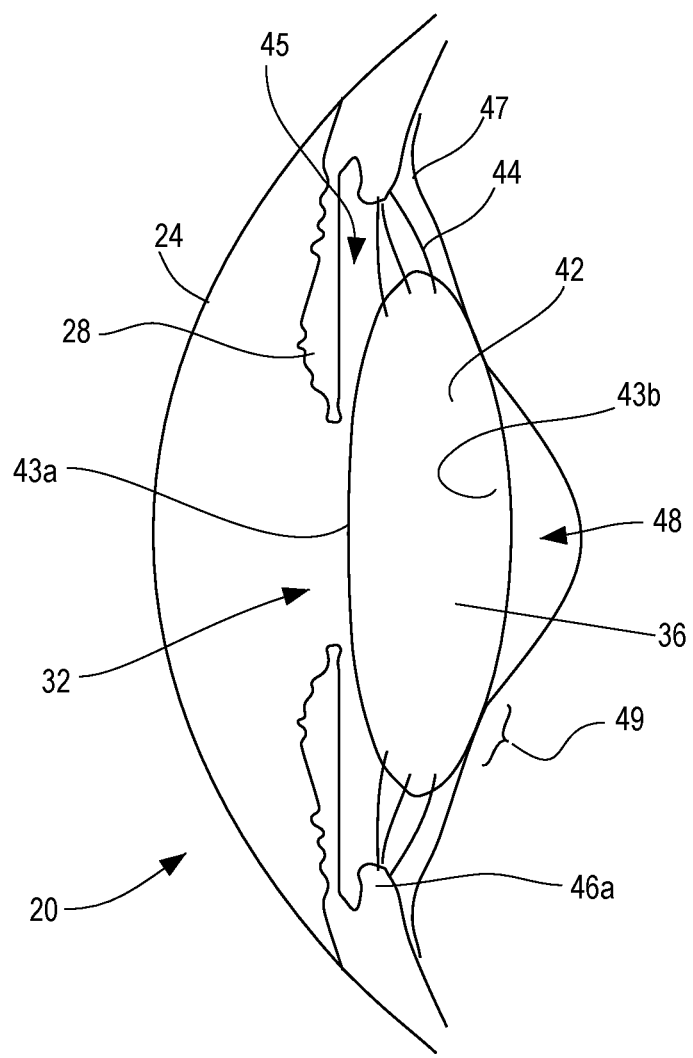
FIG. 2 is a greatly enlarged, diagrammatic view of the anterior segment of the human eye.

FIGS. 1 and 2 show a diagrammatic view of the human eye 20. Beginning at the exterior of the eye 20, the eye 20 has a protective outer layer or cornea 24 which retains the fluids or aqueous humor of the eye 20 and which focuses light. Inward of the cornea 24 is the ring-like iris 28 with an aperture or pupil 32 for restricting light reaching the lens 36. The lens 36 defines the posterior extent of the anterior segment 40 of the eye 20, sitting behind the iris 28. The lens 36 is composed of protein encased in a capsular bag 42. Supporting ligaments or zonules 44, composed of 360 degrees of attachments anterior, equatorial, and posterior, and together with Wieger's ligament (49 in FIG. 2) which defines the space of Berger (48 in FIG. 2), stabilize and center the capsular bag 42 within the eye 20. Opposing the anterior segment 40 of the eye 20 is the posterior segment 46 containing the vitreous body, optic nerves, veins, and arteries of the eye 20. The capsular bag 42 has a forward or anterior wall or portion 43a and a rearward or posterior wall or portion 44b that together retain the denser, hard lens nucleus and the surrounding, less dense lens cortex. A crevice or sulcus 45 exists between the iris 28 and the ciliary body 46a. The anterior hyaloid membrane 47 is located behind the capsular bag 42 and separates the vitreous humor of the eye from the anterior segment 40.

Figure 8:
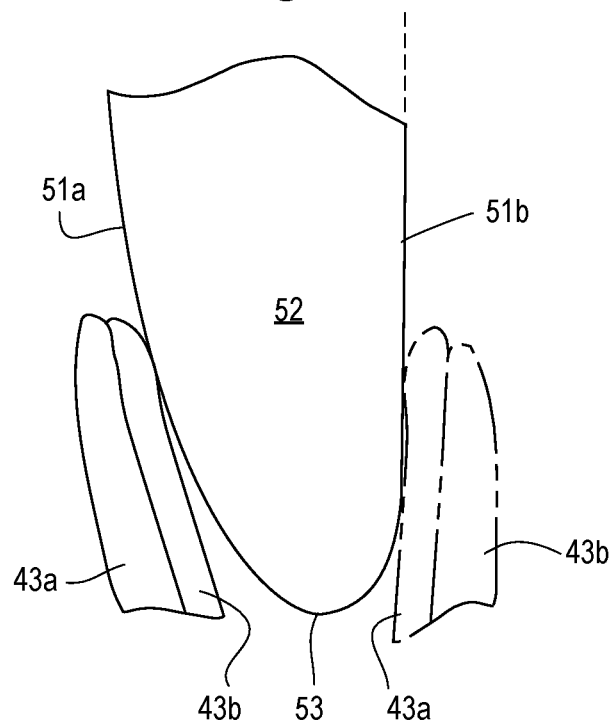
FIG. 8 is a greatly enlarged, detailed side elevation diagrammatic view of the engagement of the intraocular lens shown in FIG. 3 with the lens capsule.

As will be discussed in greater detail hereinafter, the inventors have developed advantageous methods for the prevention or minimization of the likelihood of proliferation of lens epithelial cells after the ECCE procedure discussed above. In one preferred method, a bio-compatible adhesive, such as FDA-approved synthetic polyethylene glycol hydrogel sealant sold under the trade name ReSure Sealant by Ocular Therapeutix, Inc. of Bedford Mass., is injected into the capsule after ECCE to seal the emptied anterior capsular portion 43a and posterior capsular portion 43b tight (hereinafter, the sealed portions 43a and 43b, which are illustrated in FIGS. 6-8, may collectively be referred to as "leaflets"), so that substantially no free space remains within the capsular bag 42 where aqueous and inflammatory cytokines may ingress and stimulate cell proliferation. The injection of bio-adhesives along with an anti-inflammatory agent, such as dexamethasone at low concentration of about 100 micrograms-400 micrograms per 0.05 milliliter ml or more, or in combination with an antibiotic may be done using a small 27 gauge needle either before or after IOL implantation to slowly release the medication and prevent separation of the capsular bag leaflets after the surgery and to prevent inflammation and/or infection and the growth of the anterior lens epithelial cells inside the capsule.

The bio-compatible tissue adhesive that is injected inside the leaflets 43a and 43b may require ultraviolet radiation to permanently close or seal the space between the leaflets 43a and 43b to prevent lens epithelial cell proliferation and capsular opacification. The tissue adhesive can be made to of absorbable or non-absorbable polymers. Preferably, the bio-compatible adhesive does not induce any refractive change of the IOL that is implanted subsequent to the sealing of the leaflets 43a and 43b, and the adhesive is spaced or separated completely from the IOL.

The inventors believe that sealed lens capsule leaflet (43a and 43b) may hold an IOL tight to provide a better forward and backward motion of the lens capsule and IOL, as compared to the prior art ECCE implantation methods, during the accommodation or contraction of the ciliary body muscles for seeing near objects or far objects as would happen with the normal, healthy eye.

FIGS. 3-8 show one preferred, improved intraocular lens (IOL) 50 embodying the principles of the present invention. Attendant to a phacoemulsification procedure for removal of the natural lens nucleus and cortex from the capsular bag 42, the IOL 50 is especially suited for the implantation techniques that will be discussed in detail hereinafter. The lens 50 has a central lens body or optic 52 made from a biocompatible transparent polymeric material such as PMMA, silicone, hydrogel, or acrylic, and portions of which may be hydrophobic, hydrophilic, or amphiphilic, or a combination thereof.

With reference now to FIG. 8, the central lens body 52 has a first and second, opposite anterior (anterior with respect to the frontal plane) and posterior (posterior with respect to the frontal plane) surfaces 51a and 51b, respectively. The posterior surface 51b of the lens body 52 generally resides in a plane 55. The central lens body 52 has a suitable cross-sectional configuration for providing vision correction for the patient, which is known in the art. The anterior surface 51a and posterior surface 51b of the central lens body 52 meet or join in a rounded peripheral or side surface 53. As will be discussed in detail hereinafter, one or more of the surfaces of the lens body 52 are especially suited for engaging the sealed leaflets 43a and 43b of the capsular bag 42. To this end, one or more of the surfaces 51a, 51b, and/or 53 may be treated with a surface treatment or applied layer of a different material, or made from a material that is different from the remaining portion of the lens body 52, to enhance sealing of the lens body 52 with the sealed leaflets 43a and 43b.

The lens body 52 may have one or more surfaces of a varying degree of convexity depending on the need for correction to the patient's vision. The lens body 52 may have a toric or spherical shape, a positive dioptric power, or possess multiple focal points to correct a patient's vision as is known in the art.

Figure 3:
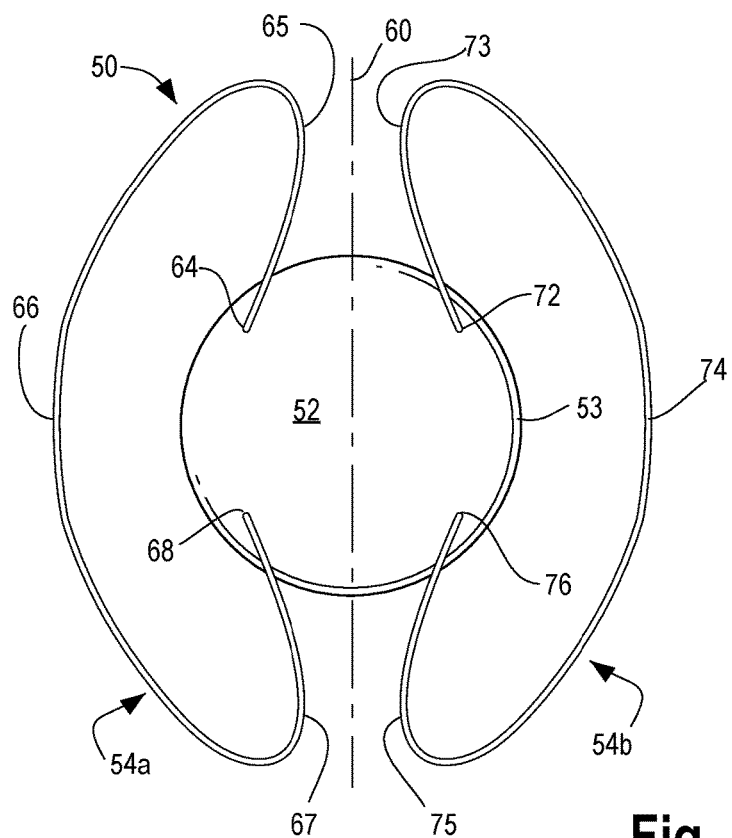
FIG. 3 is an enlarged, top plan view of an embodiment of an improved intraocular lens according to the present invention.

Referring to FIG. 3, the lens 50 further preferably includes a pair of haptics 54a and 54b extending from the central lens body 52 in a bi-lobular or "butterfly" configuration that surrounds the circular optic in a semi-oval fashion creating two wings that connect the superior portion of the lens body 52 to its inferior part. The haptics 53a and 54b are inserted or connected to the lens body 52 in either (i) a parallel fashion with respect to the plane of the posterior surface 51b of the lens body 52, or (ii) an angled or offset fashion with respect to the plane 55 defined by the posterior surface 51b of the lens body 52, producing a slight separation or angle between the plane 55 of the posterior surface 51b of the lens body 52 and attachment points of the haptics 54a and 54b, whereby the leaflets 43a and 43b of the lens capsule 42 may sit comfortably against the lens 50 and contribute to the closure of the space between the anterior and the posterior capsule (FIG. 6 or 7) to prevent or at least minimize the likelihood of capsular opacification, tilt and provide balance and stability to the IOL 50 within the eye.

With reference to FIG. 3, the haptics 54a and 54b are generally symmetric about a central axis 60 of the IOL 50. The path of the haptic 54a, which is generally kidney shaped, includes a first point of connection 64 to the lens body 52 and extends toward the central axis 60 before curving back away from the central axis 60 at a first distal end 65. From the first distal end 65, the haptic 54a extends away from the central axis 60 in an arc toward a medial point 66, at which point the haptic 54a curves back toward the central axis 60. The haptic 54a includes a second distal end 67 where the haptic 54a curves back away from the central axis 60 to a second point of connection 68.

Still referring to FIG. 3, the path of the haptic 54b includes a first point of connection 72 to the lens body 52 and extends toward the central axis 60 before curving back away from the central axis 60 at a first distal end 73. From the first distal end 73, the haptic 54b extends away from the central axis 60 in an arc toward a medial point 74, at which point the haptic 54b curves back toward the central axis 60. The haptic 54b includes a second distal end 75 where the haptic 54b curves back away from the central axis 60 to a second point of connection 76.

As will be discussed below, the haptics 54a and 54b have a configuration that may be advantageously engageable with the ciliary body 46a for stabilizing the lens 50 (FIG. 6). Alternatively, the haptics 54a and 54b may be located behind the leaflets 43a and 43b for stabilizing the lens 50 (FIG. 7).

Figure 4:
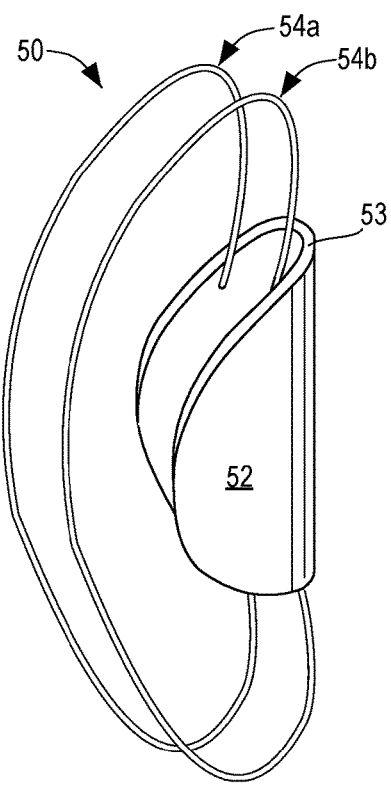
FIG. 4 is an enlarged, perspective view of the intraocular lens shown in FIG. 3 in a folded configuration prior to being implanted within the human eye.
Figure 5:
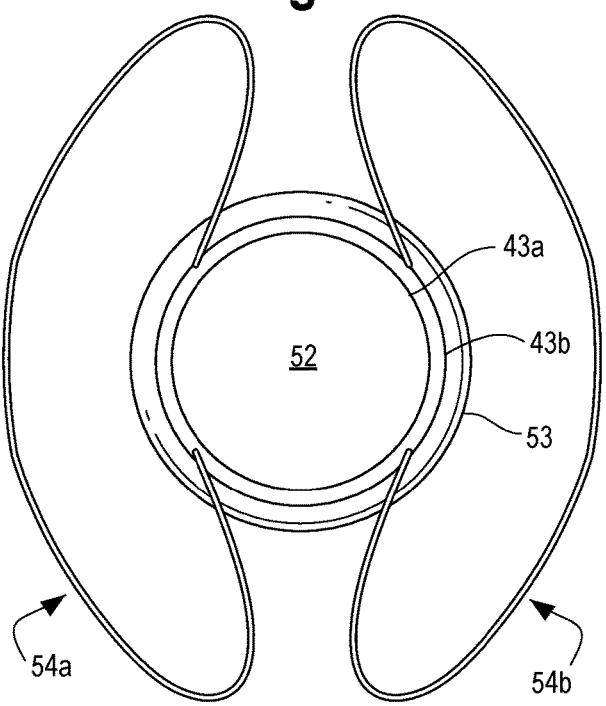
FIG. 5 is an enlarged, top plan diagrammatic view of the intraocular lens shown in FIG. 3 implanted within the human eye.

With reference to FIG. 4, the lens 50 would be implanted using standard or customized injectable technology by folding it and injecting it in the desired location within the eye along with a viscoelastic material through a very small incision in the cornea 24. The viscoelastics would then be washed away with saline solution after implantation to prevent rise in the intraocular pressure.

With reference now to FIG. 6, in one preferred configuration of implantation of the IOL 50, the lens body 52 or optic is positioned in the space of Berger 48, such that the leaflets 43a and 43b lie overtop of the lens body 52. In this configuration, the haptics 54a and 54b lie substantially (e.g., almost entirely) over the anterior capsule 43a, and may lie on the zonulas 44 (if intact), or may reach the ciliary body 46a to make the IOL 50 independent from the lens capsule 42 in case the weak or ruptured zonulas 44. The haptics 54a and 54b may reach or touch the sulcus 45 between the ciliary body 46a and the iris 28 (not illustrated). Contact between the haptics 54a and 54b with the ciliary body 46a is also limited to two points on each side of the lens body 52 to limit the undesirable uncontrolled penetration of the lens haptic 54a and 54b inside the ciliary body 46a, which could cause bleeding or irritation or inflammation in the eye. The inventors believe that the configuration of the bi-lobe haptics 54a and 54b may provide a better-balanced lens optic or lens body 52 and create a better centration for the lens body 52 to prevent or minimize the likelihood of tilting of the IOL 50.

With reference now to FIG. 7, in one alternative configuration of implantation of the IOL 50, the lens body 52 or optic is positioned behind the iris 28 such that it lies overtop of the leaflets 43a and 43b to balance the lens optic or lens body 52 and create a better centration for the lens body 52 to prevent or minimize the likelihood of tilting of the IOL 50.

The inventors believe that in the IOL 50 implantation configuration illustrated in FIGS. 5, 6, 7, and 8, the lens body 52 or optic acts like a plug to close the opening in the posterior or anterior chamber preventing penetration of the vitreous into the anterior chamber, which would have undesirable complications.

In an alternative configuration, not illustrated, the IOL 50 is implanted such that lens body 52 is located in an intermediate position, within the lens capsule 42.

The inventors of the present invention believe that the IOL 50 and the methods of implantation described above may be beneficial to prevent or at least minimize the likelihood of secondary cataract of the posterior portion 43b of the lens capsule 42 such that duplicative or remedial surgeries, common with prior art surgical procedures and lens designs, may be minimized or eliminated over the lifetime of the patient.

In another embodiment, the IOL 50 can act as an additional, or secondary IOL to a normal crystalline lens to correct either a high myopic eye In another embodiment, the IOL 50 can be positioned over an existing IOL in a previously operated upon eye to compensate for the existing refractive errors of the eye eliminating the need for a complex surgery of removing an existing IOL from its capsular bag and eliminating or reducing post-operative trauma contributing to a faster visual rehabilitation and wound healing.

Figure 9:
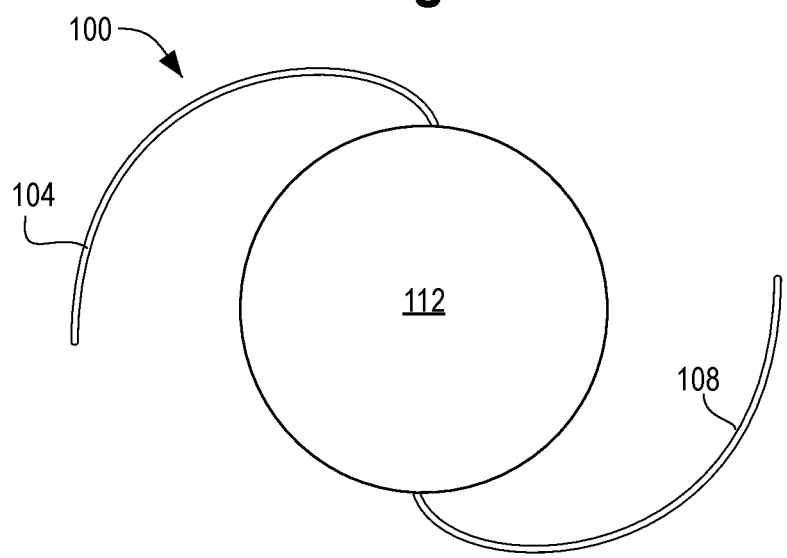
FIG. 9 illustrates a top plan view of a secondary intraocular lens that may be implanted overtop of the intraocular lens shown in FIG. 3.

In one embodiment, the surgical methods disclosed herein may be modified for younger patients, adults or children, in whom the eye grows and requires a different refractive correction over time. In such a modified method, a secondary IOL such as the IOL 100 illustrated in FIG. 9 is implanted over, e.g., in front of, the initially implanted intraocular lens 50. The secondary IOL 100 includes a pair of haptics 104 and 108 which have discrete endpoints or poles, and which are not in the form of loops. The secondary IOL 100 further includes an optic or lens body 112, which may be a plus, a minus or a toric IOL depending on the patient's need. The secondary IOL 100 is preferably implanted with its haptics 104 and 108 positioned generally 90 degrees relative to the haptics 54a and 54b of the inventive IOL 50 (e.g., generally extending perpendicular to the central axis 60) such that the haptics 104 and 108 are located over the existing crystalline lens or zonulae 44 in the posterior chamber behind the iris 28. The secondary IOL 100 and the IOL 50 are separated or spaced from each other at all times.

The secondary IOL 100 is generally self-maintained in the eye due to the structure of its haptics 104 and 108 and the structure of the eye, and the secondary IOL 100 does not adhere to the lens capsule 42. Thus, the secondary IOL 100 can be easily removed or replaced without tearing or cutting the tissue of the eye.

The stacked positions of these two IOLS 50 and 100 might have an implication in creating an accommodative lens where the lenses get closer to each other and separate from each other depending on the accommodative process and contraction of the ciliary muscles and their pull on the lens, zonulas/capsule puling it forward or relaxing it backward.

In another embodiment of the present invention, one can modify the index of refraction of the IOL 50 or 100 non-invasively by changing its index of refraction using a femtosecond laser as needed throughout the patient's life. In some applications, the IOL 50 or 100 has a fixed refractive power. However, the refractive index of the IOL 50 or 100 can be modified to create bifocal, trifocal, multifocal or toric lens prior to the surgery or afterward using nanojoule pulses of a femtosecond laser applied to the surface of the IOL 50 or 100. The IOL 50 or 100 may be provided with an extra soft polymeric surface such as crosslinked collagen. The inventors believe that such a lens would prevent or at least minimize the likelihood of the problems associated with multi focal lenses which include, tilt, capsular opacification, off-axis positioning and the difficulty of lens exchange.

In one form, the surface of the IOL 50 or 100 is exposed to low energy nanojoule femtosecond pulses to modify the index or the refraction of the lens 112 to the desired power and the control of a wave front technology unit to accurately provide accurate femtosecond pulses to the lens surface and create an emmetropic refraction or multifocal refraction as desired for the patents' need.

The invention claimed is:

1. An intraocular lens for implantation into a human eye, the human eye having a lens capsule with an anterior portion and a posterior portion, the lens capsule having a cortex and a natural lens removed therefrom, the lens capsule having a capsulotomy in each of the anterior and posterior portions, and the lens capsule anterior and posterior portions sealed to each other, the intraocular lens comprising:
    a lens body for providing vision correction for a patient, said lens body defining an anterior surface and a posterior surface, said posterior surface defining a first plane;
    a pair of haptics extending from said lens body, each one of said pair of haptics having a kidney shaped, lobular configuration forming a closed loop with (i) a first end connected to said lens body at a first location on said lens body, and (ii) a second end connected to said lens body at a second location on said lens body, said second location on said lens body being spaced from said first location on said lens body;
    wherein said lens body and said pair of haptics have a folded configuration for being implanted in the human eye;
    wherein said lens body and said pair of haptics have at least one of the following deployed configurations: (i) a first deployed configuration wherein said lens body is positioned in the eye such that the sealed anterior and posterior portions of the lens capsule contact said anterior surface of said lens body; or (ii) a second deployed configuration wherein said lens body is positioned in the eye such that the sealed anterior and posterior portions of the lens capsule contact said posterior surface of said lens body; and
    wherein said lens body defines a central axis extending between said pair of haptics to divide said lens body into symmetric halves, each one of said halves containing one haptic of said pair of haptics;
    a first haptic of said pair of haptics includes
        a first point of connection to said lens body and a second point of connection to said lens body, said first haptic defining a path from said first point of connection to said lens body to said second point of connection to said lens body whereby said first haptic extends from said first point of connection to said lens body radially toward said central axis and curves back radially away from said central axis at a first distal end, from said first distal end said first haptic extends radially away from said central axis in an arc toward a medial point along a medial length of said first haptic, from said medial point said first haptic curves back radially toward said central axis to a second distal end, at said second distal end said first haptic curves back radially away from the central axis to said second point of connection, said medial length being greater than a diameter of said lens body and said medial length being substantially within a second plane parallel to said first plane, said second plane being anterior of said anterior surface of said lens body when said lens body is positioned to contact the posterior surface of the sealed capsule or said second plane being posterior of said posterior surface of the lens body when said lens body is positioned to contact the anterior surface of the sealed capsule; and
    a second haptic of said pair of haptics symmetric to said first haptic about said central axis of said lens body.

2. The intraocular lens in accordance with claim 1, wherein said lens body is formed from a transparent polymer with a surface treatment to make said lens body hydrophobic, hydrophilic, or amphiphilic.

3. The intraocular lens in accordance with claim 1 in combination with a secondary intraocular lens, said combination arranged in a non-contacting, spaced-apart configuration.

4. The intraocular lens in accordance with claim 1, wherein a first portion of said lens body is formed from a first polymer and a second portion of said lens body is formed from a second polymer, said second polymer being softer than said first polymer.

5. A method of implanting an intraocular lens in a human eye having a lens capsule with an anterior portion and a posterior portion, a natural lens nucleus, and a cortex, the method comprising steps of:
    obtaining the intraocular lens, said intraocular lens including:
    a lens body for providing vision correction for a patient, said lens body defining an anterior surface and a posterior surface, said posterior surface defining a first plane;
    a pair of haptics extending from said lens body, each one of said pair of haptics having a kidney shaped, lobular configuration forming a closed loop with (i) a first end connected to said lens body at a first location on said lens body, and (ii) a second end connected to said lens body at a second location on said lens body, said second location on said lens body being spaced from said first location on said lens body;
    wherein said lens body and said pair of haptics have a folded configuration for being implanted in the human eye;
    wherein said lens body and said pair of haptics have at least one of the following deployed configurations: (i) a first deployed configuration wherein said lens body is positioned in the eye such that sealed anterior and posterior portions of the lens capsule contact said anterior surface of said lens body; or (ii) a second deployed configuration wherein said lens body is positioned in the eye such that the sealed anterior and posterior portions of the lens capsule contact said posterior surface of said lens body; and wherein said lens body defines a central axis extending between said pair of haptics to divide said lens body into symmetric halves, each one of said halves containing one haptic of said pair of haptics;

a first haptic of said pair of haptics includes a first point of connection to said lens body and a second point of connection to said lens body, said first haptic defining a path from said first point of connection to said lens body to said second point of connection to said lens body whereby said first haptic extends from said first point of connection to said lens body radially toward said central axis and curves back radially away from said central axis at a first distal end, from said first distal end said first haptic extends radially away from said central axis in an arc toward a medial point along a medial length of said first haptic, from said medial point said first haptic curves back radially toward said central axis to a second distal end, at said second distal end said first haptic curves back radially away from the central axis to said second point of connection, said medial length being greater than a diameter of said lens body and said medial length being substantially within a second plane parallel to said first plane, said second plane being anterior of said anterior surface of said lens body when said lens body is positioned to contact the posterior surface of the sealed capsule or said second plane being posterior of said posterior surface of the lens body when said lens body is positioned to contact the anterior surface of the sealed capsule; and a second haptic of said pair of haptics is symmetric to said first haptic about said central axis of said lens body performing a capsulotomy of the anterior portion of the lens capsule;

removing the natural lens nucleus and the cortex from the lens capsule;

performing a capsulotomy of the posterior portion of the lens capsule;

and the sealed anterior and posterior portions formed by sealing the anterior and posterior portions of the lens capsule together.

6. The method of claim 5 further comprising a step of implanting said intraocular lens to locate said lens body in Berger's space such that the sealed anterior and posterior portions of the lens capsule contact said anterior surface of said lens body.

7. The method of claim 5 further comprising a step of implanting said intraocular lens to locate said lens body such that the sealed anterior and posterior portions of the lens capsule contact said posterior surface of said lens body.

8. The method of claim 5 wherein the step of sealing together said anterior and said posterior portions of said lens capsule includes injecting a bio-compatible adhesive between said anterior and said posterior portions of said lens capsule.

9. The method of claim 8 further comprising a step of applying ultraviolet radiation to said adhesive between said sealed anterior and said posterior portions of said lens capsule.

10. The method of claim 8 further comprising the step of injecting an anti-inflammatory agent with said adhesive.

11. The method of claim 5 further comprising steps of: (a) implanting said intraocular to locate said lens body against said sealed anterior and posterior portions of said lens capsule; and (b) implanting a second intraocular lens in front of said first intraocular lens such that said first and said second intraocular lenses are in a non-contacting relationship.

12. The method of claim 5 further comprising a step of applying a femtosecond laser to the lens body to change its refractive index.

* * * * *